United States Patent [19]

Masaki

[11] Patent Number: 5,213,567
[45] Date of Patent: May 25, 1993

[54] DEVICE FOR PREVENTING ABRASIVE INJURY FROM SKIN AND FAT ASPIRATING DEVICE AND FAT ASPIRATING METHOD

[76] Inventor: Nobuyuki Masaki, c/o Kyoritsu Cosmetic Surgery, Tokyo Sogo Biyo Bld., 3F 4-18-4, Shiba, Minato-ku Tokyo 108, Japan

[21] Appl. No.: 752,603
[22] PCT Filed: Dec. 19, 1990
[86] PCT No.: PCT/JP90/01654
  § 371 Date: Aug. 14, 1991
  § 102(e) Date: Aug. 14, 1991
[87] PCT Pub. No.: WO91/08780
  PCT Pub. Date: Jun. 27, 1991

[30] Foreign Application Priority Data

Dec. 20, 1989 [JP] Japan .................................. 1-330131

[51] Int. Cl.⁵ .............................................. A61N 1/30
[52] U.S. Cl. ...................................... 604/19; 604/175; 604/902
[58] Field of Search ................... 604/19, 21, 174, 175, 604/164, 264, 902

[56] References Cited

U.S. PATENT DOCUMENTS

| | | | |
|---|---|---|---|
| 4,536,180 | 8/1985 | Johnson | 604/902 |
| 4,578,063 | 3/1986 | Inman et al. | 604/244 |
| 4,781,694 | 11/1988 | Branemark et al. | 604/175 |
| 4,815,462 | 3/1989 | Clark | 604/902 |
| 4,863,438 | 9/1989 | Gauderer et al. | 604/175 |
| 4,936,826 | 6/1990 | Amarasinghe | 604/175 |
| 4,944,732 | 7/1990 | Russo | 604/175 |
| 5,013,300 | 5/1991 | Williams | 604/902 |

*Primary Examiner*—Stephen C. Pellegrino
*Assistant Examiner*—Michael Rafa
*Attorney, Agent, or Firm*—Herbert Dubno; Yuri Kateshou

[57] ABSTRACT

The device for preventing abrasive injury from skin in the fat aspirating device is inserted into a biological body and have a bore portion a pipe with a fat aspirating tube 11 capable of being inserted into a biological body through the bore portion and an aperture communicated with the bore portion, as well as a flange 2 connected to the pipe and directly facing the skin of the biological body when the pipe.

11 Claims, 5 Drawing Sheets

DEVICE FOR PREVENTING ABRASIVE INJURY FROM SKIN AND FAT ASPIRATING DEVICE AND FAT ASPIRATING METHOD

CROSS REFERENCE TO RELATED APPLICATIONS

This application is a National Phase of PCT/JP90/01654 filed Dec. 19, 1990 and based upon a Japanese International Application 330131 1989 filed Dec. 20, 1989.

Field of Invention

The present invention relates to a device for preventing abrasive injury from skin to be used in the case of inserting a bar-like body such as cannula into a biological body including human bodies for treatment and examination, a fat aspirating device for aspirating a fatty fraction in human bodies, and a fat aspirating method.

Background Art

As one of the methods to treat severe obesity and adiposis, there is included a method to remove fat per se surgically. The fat aspirating method reported by Louise in 1978, France, in particular, has been distinctly common since the incisions on skin according to the method are relatively small and the method promises a reliable therapeutic effect.

According to the fat aspirating method, there is employed a fat aspirating device provided with a metallic fat aspirating tube having pores in the vicinity of the tip thereof and of a several-mm diameter, for example, 2 to 3 mm, and with a vacuum aspirating means being connected with the fat aspirating tube and producing a negative pressure.

Fat aspiration is carried out by incising skin at a relatively small size, inserting a fat aspirating tube through the incision into a fatty layer inside a body, and removing fat, through the pores on the vicinity of the tip of the fat aspirating tube, outside the body by means of a vacuum aspirating means. Such fat aspiration is not carried out while fixing a fat aspirating tube at a predetermined position, but the tube is manually operated to make round-trip motion at a rate of approximately 80 to 120 times per minute. One-hour requirement for aspirating fat in belly, for example, forces a fat aspirating tube to make round-trip motion at a rate of about 4800 to 7200 times through the insertion site of the fat aspirating tube, i.e. through the incision site.

Accordingly, on the skin on the circumference of the incision site damages are caused such as, for example, pressure-induced abrasion, abrasive injury, and abrasion, and the size of the incision site is more enlarged than the initial size thereof for example by a factor of 1.5, leading to severe damage to tissues. Hence, the scar of the incision site is apparently identified and marked after the operation.

Objects of the Invention

The object of the present invention is thus to provide a device for preventing abrasive injury from skin on the circumference of an insertion site of a bar-like body such as cannula to be inserted into a biological body and be made to move.

Another object of the present invention is to provide a fat aspirating device and a fat aspirating method, capable of performing fat aspiration under the condition to insert a fat aspirating tube while preventing the abrasive injury of skin.

Summary of the Invention

The device according to one embodiment of the present invention, is provided with a pipe inserted into a biological body and having a bore portion through which a bar-like body is inserted into a biological body, the pipe is provided with a flange having an aperture communicated with the bore portion and connected with the pipe and facing the skin of the biological body when the pipe is inserted into the biological body.

According to the present invention the device thus structured is inserted into a biological body but does not directly contact to skin in order to protect skin of the biological body and the vicinity thereof. As a result the abrasive injury on the skin due to the motion of the bar-like body can be prevented. Hence, the scar on the skin at the insertion part of the bar-like body after surgery is of a light degree, and the scar is not identified, apparently.

According to another embodiment of the invention, a fat aspirating device comprises a fat aspirating tube having pores in the vicinity of the tip thereof, a fat reservoir means being connected to the fat aspirating tube, a vacuum aspirating means being connected to the fat reservoir means, a device for preventing abrasive injury from skin is provided with a pipe inserted into a biological body and having a bore portion through which a bar-like body is inserted into the biological body, and with a flange having an aperture communicated with the bore portion and connected with the pipe to face the skin of the biological body when the pipe is inserted into the biological body.

According to the present invention, the fat aspirating tube to be inserted into a biological body does not directly contact to skin thereby protecting skin of the biological body and the vicinity thereof, so that even the repetitive round-trip motion of the fat aspirating tube for fat aspiration does not cause abrasive injury on skin.

According to still another embodiment of the invention, the fat aspirating method comprises individual steps consisting of a step for incising skin of a biological body, a step for inserting the pipe of the device for preventing abrasive injury from skin through the incision site into the biological body, a step for inserting the fat aspirating tube through the aperture of the flange of the device for preventing abrasive injury from skin into the biological body, a step for aspirating fat inside the biological body by means of the vacuum aspirating means while the fat aspirating tube makes round-trip motion in the biological body, and a step for closing the incision site after removing the device for preventing abrasive injury outside the biological body after the termination of the fat aspiration.

According to the present invention thus structured, fat thus fat from skin. Hence, the scar on the skin at the incision site after surgery is of a light degree, and the scar is not identified, apparently.

BRIEF DESCRIPTION OF THE DRAWING

The above and other objects, features and advantages of my invention will become more readily apparent from the following description, reference being made to the accompanying highly diagrammatic drawing in which.

SPECIFIC DESCRIPTION

Figure 1:
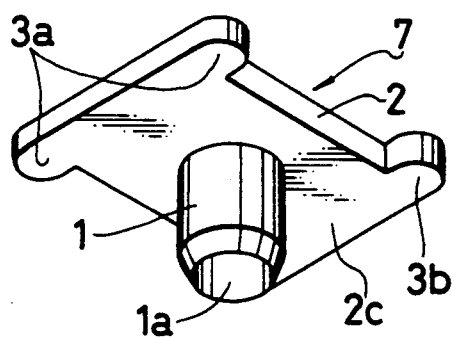
FIG. 1 is a perspective view of a device for preventing abrasive injury from skin in a fat aspirating device according to a first embodiment of the present invention.
Figure 2:
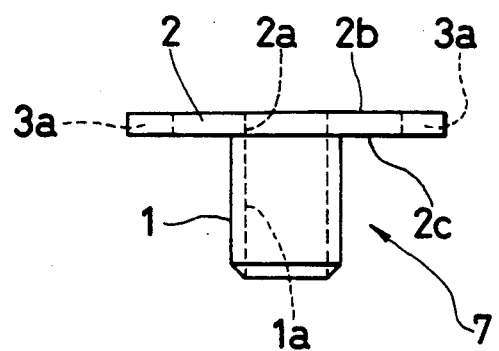
FIG. 2 is a side view of the device for preventing abrasive injury from skin shown in FIG. 1.
Figure 3:
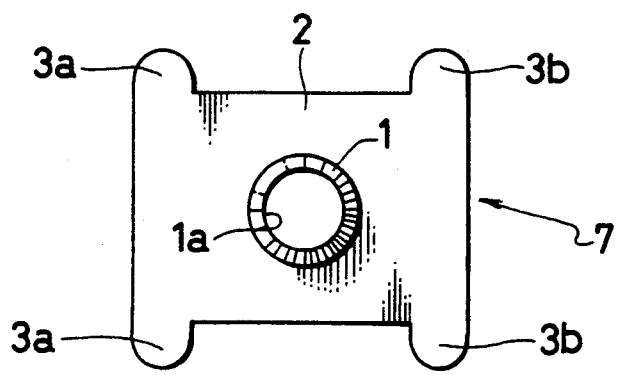
FIG. 3 is a front view of the device for preventing abrasive injury from skin according to FIG. 1.

One of the embodiments of a fat aspirating device shown in FIGS. 1 to 3 is, a device for preventing abrasive injury from skin 7 used in the fat aspirating device is provided with a pipe 1 having a bore portion 1a and a flange 2 having flange surfaces 2b, 2c and being connected to the pipe 1. The pipe 1 is connected to the flange surface 2c almost at right angle. The device comprises the integrally molded pipe 1 and flange 2 from polytetrafluoroethylene (product name; teflon).

A fat aspirating tube 11 (FIG. 6) is inserted into the bore portion 1a as described hereinafter. The tip of the pipe 1 is through chamfering. An aperture 2a communicating with the bore portion 1a is formed in the flange 2, and through the aperture 2a, the fat aspirating tube 11 is inserted into a biological body. A pair of protrusions 3a facing each other and a similar pair of protrusions 3b are individually placed on 4 corners of the flange 2.

These protrusions 3a, 3b are for controlling the position of the thread for fixing the device on skin of a biological body, and they may be in configuration of other forms, for example, notch-like form.

Figure 4:
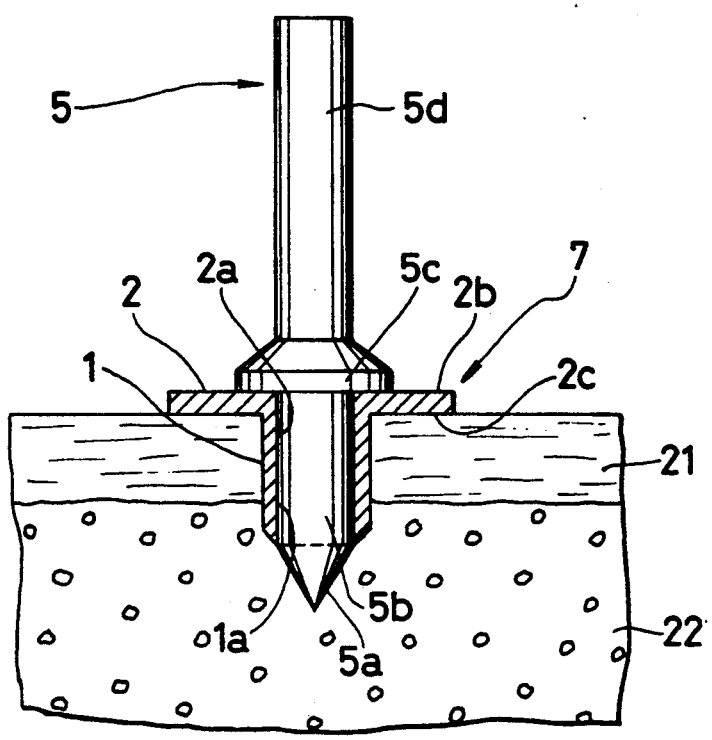
FIG. 4 is a sectional view showing the device for preventing abrasive injury from skin according to FIG. 1 inserted together with an auxiliary device for insertion through skin into a biological body.

FIG. 4 shows of skin 7 into a biological body. The auxiliary device for insertion 5 comprises tip 5a in conical form, an insertion part 5b to be inserted into the bore portion 1a of the pipe 1 of the device, a stopper 5c for controlling the position of the tip 5a when inserted into the bore portion 1a, and a grip 5d to grip the auxiliary device for insertion 5. The auxiliary device for insertion 5 is constructed from integrally molded polytetrafluoroethylene.

The auxiliary device for insertion 5, described above, is used in the state in which the device is inserted into the device on inserting the pipe 1 into a biological body. The auxiliary device for insertion 5 is inserted from tip 5a into the aperture 2a and the bore portion 1a of the device, so the surface of stopper 5c directly faces the flange surface 2b. The tip 5a is in the state of being exposed outside the tip of the pipe 1 of the device for preventing abrasive injury from skin 7.

The device for preventing abrasive injury from skin 7 with the auxiliary device for insertion 5 and inserted into a biological body and fixed therein as follows. That is, a relatively small incision is made on skin, and the device for preventing abrasive injury from skin 7 is inserted together with the auxiliary device 5 through the incision on the skin. As the tip 5a of the auxiliary device 5 is in conical form, the device for preventing abrasive injury from skin 7 can be extremely easily inserted into a biological body. Owing to the use of the auxiliary device 5, there is provided greater protection for the tissue in the vicinity of the skin at the insertion site of the device for preventing abrasive injury of skin 7 than in the case without the use thereof.

As shown in FIG. 4, the pipe 1 of the device should be inserted until the flange surface 2c directly faces the surface of skin 21, so the pipe 1 is embedded inside the biological body almost perpendicularly toward the surface of the skin 21.

Figure 5:
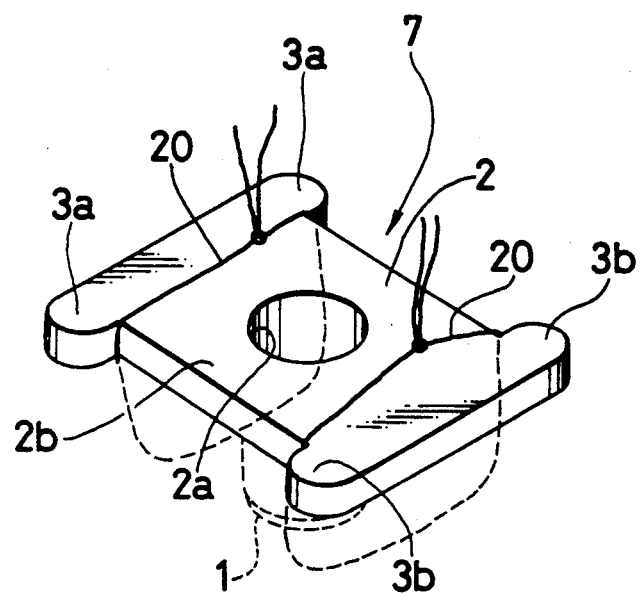
FIG. 5 is a perspective view of the device for preventing abrasive injury from skin according to FIG. 1 fixed on skin by means of thread.

After the auxiliary device 5 is then drawn out of the device for preventing abrasive injury from skin 7, the flange 2 of the device is fixed at 2 parts by means of thread 20 as shown in FIG. 5. The thread 20 is joined together on the flange surface 2b after passing inside the biological body. A pair of protrusions 3a and another pair of protrusions 3b control the position of the thread 20, so that there is no possible removal of the thread from the flange 2.

Figure 6:
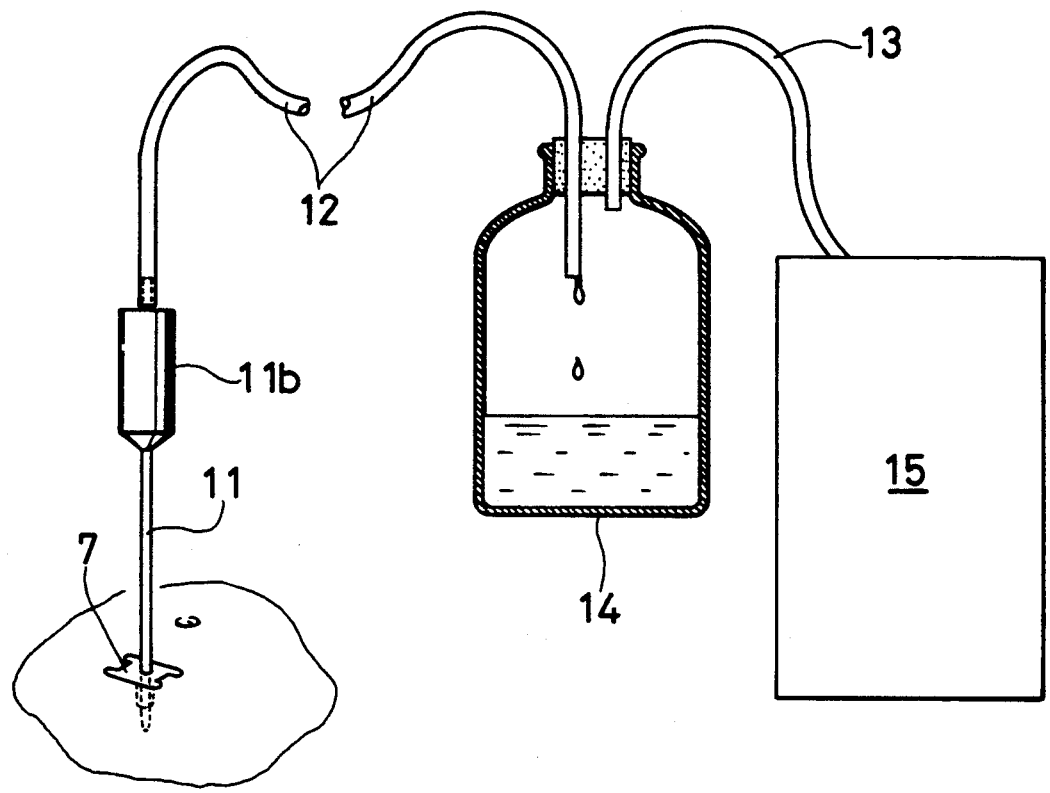
FIG. 6 is a view schematically depicting the overall fat aspirating device.

As shown in FIG. 6, the fat aspirating device of the present example comprises, besides the device, a fat aspirating tube 11 inserted into a biological body, a bottle 14 to reserve the fat aspirated from inside the biological body, a vacuum aspirating means 15 generating a negative pressure, and flexible tubes 12, 13 for connecting them mutually. There can be employed such conventionally known means as the vacuum aspirating means 15.

Figure 7:
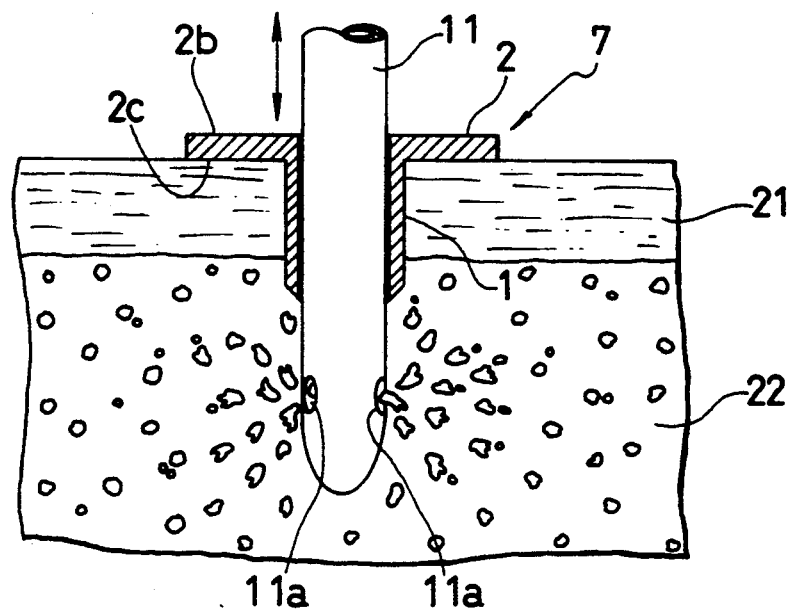
FIG. 7 is a sectional view of the fat aspirating tube inserted through the device for preventing abrasive injury from skin according to FIG. 1, into fatty layer inside a biological body to aspirate fat.
Figure 8:
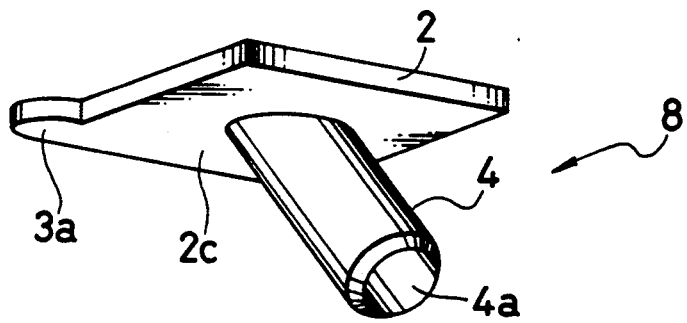
FIG. 8 is a perspective view of the device for preventing abrasive injury from skin in a fat aspirating device according to another embodiment of the present invention.

In the vicinity of its tip to be inserted in a biological body, the fat aspirating tube 11 has pore 11a as shown in FIG. 7, as well as a grip 11b to hold the fat aspirating tube 11 with hands. Pore 11a may be in single or plural number.

A preventing means for preventing the direct absorption of the fat aspirated from inside a biological body into a vacuum aspirating means 15 can be appropriately placed between the bottle 14 and the vacuum aspirating means 15.

According to the fat aspirating device insofar mentioned, the fat aspirating tube 11 as shown in FIG. 7 is inserted into the fat layer 22 in a biological body, from the tip having pores 11a through the aperture 2a and the bore portion 1a of the device.

When the vacuum aspirating means 15 initiates operation, the pressure inside the bottle 14 gets negative through a tube 13. Through a tube 12 and a fat aspirating tube 11, the pressure in the vicinity of the pores 11a subsequently gets negative, so that the fat in the vicinity of the pores 11a is aspirated through the pores 11a, passing in the fat aspirating tube 11 and the tube 12, to reach the bottle 14.

The fat aspirating tube 11 makes round-trip motion in the direction of the arrow shown in FIG. 7, until the end of the predetermined fat aspiration.

Even after the repeated round-trip motion, the circumference of the dermal incision never directly contacts to the fat aspirating tube 11 on the surface of skin 21 and in the vicinity of the surface, which is different from conventional manners, so that no abrasive injury might be caused on the circumference of the dermal incision.

After the end of fat aspiration, the device is removed from inside the biological body, and the vulnus of the incised site of the skin is then closed by subcutaneous suture. In some case, tape fixation is just enough with no need of subcutaneous suture. As no abrasive injury is present on the circumference of the incised site of the skin, the vulnus is remarkably cured with a slight degree of scars not apparently identified at the incised site of the skin.

Preferably, the device for preventing abrasive injury from skin 7 according to the above-described embodiment is used in the sites with a relatively thick fat layer such as those in abdomen.

As the condition to be considered for selecting materials constituting the device and an auxiliary device for insertion 5, there can be mentioned the following; no adverse effects on biological bodies, no abrasion due to the round-trip motion of the fat aspirating tube, no abrasion of the fat aspirating device, relative stability toward temperatures, and possibility of integral molding at a low cost and the like. The materials satisfying these conditions are preferable, for example, polytetrafluoroethylene and silicone resin.

According to the embodiment a fat aspirating device is similar to that described above while the device for preventing abrasive injury of skin 8 is different from the device shown in FIGS. 1 to 3. The identical parts to those of the device for preventing abrasive injury from skin 7 are marked with the same symbols and the explanation thereof is not presented.

The device shown in FIGS. 8 to 12 is characterized by the pipe 4 with a bore portion 4a through which a fat aspirating tube 11 can be inserted at an angle different from a right one to a flange surface 2c. The slanting angle θ made by the axial direction of the pipe 4 and the flange surface 2c (shown in FIG. 9) can be appropriately determined. Therefore, the device can be inserted into a biological body, while the pipe 4 thereof is inclined to the dermal surface.

Figure 9:
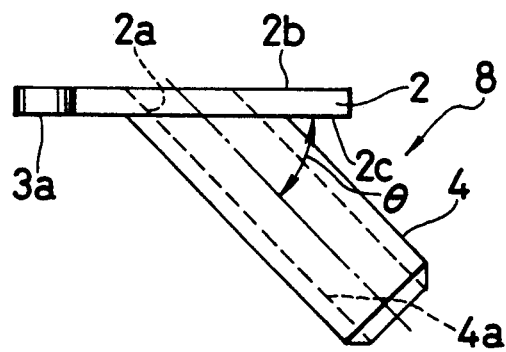
FIG. 9 is a side view of the device according to FIG. 8.
Figure 10:
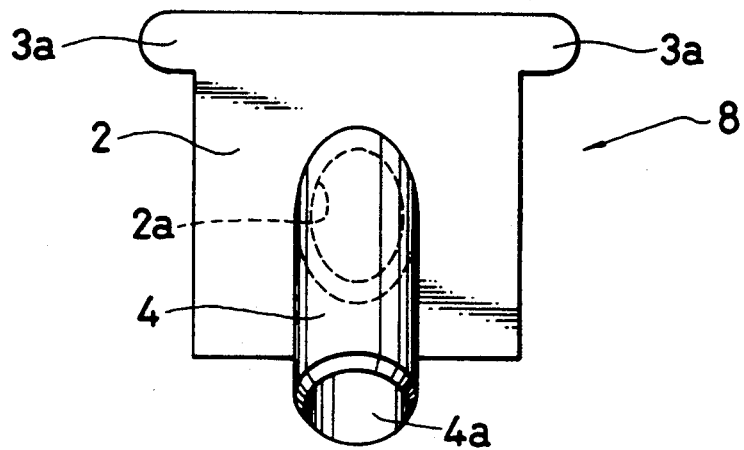
FIG. 10 is a front view of the device according to FIG. 8.

As shown in FIGS. 9 and 10, on one side of the flange 2 as the inverse side of the slanting direction of the pipe 4, i.e. on the two corners of the flange 2 in the direction with an obtuse angle between the axis of the pipe 4 and the flange surface 2c, there are mounted a pair of protrusions 3a. On the two corners of the flange 2 in the direction with a sharp angle, there are omitted protrusions but there may or may not be mounted protrusions similarly as in Example 1.

Figure 11:
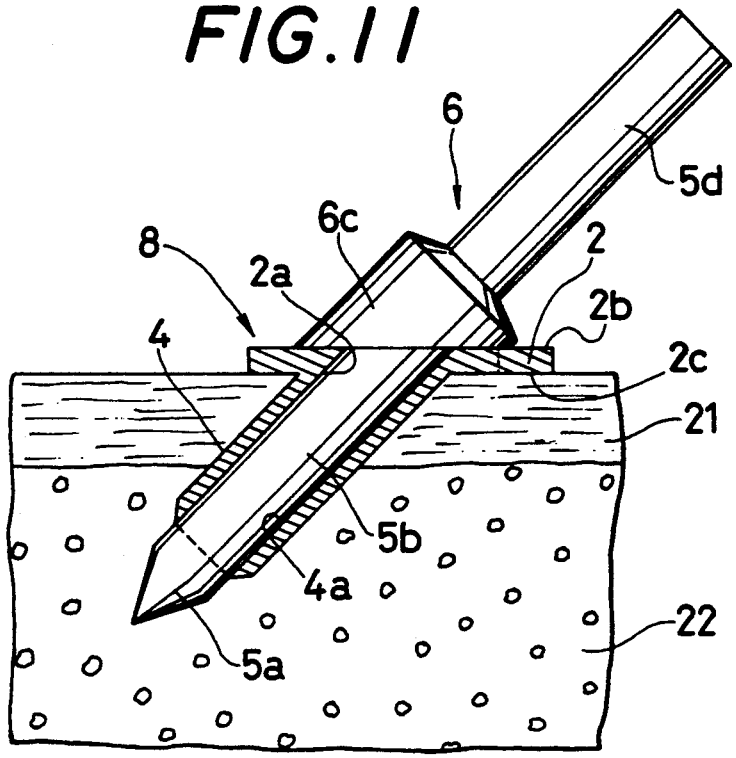
FIG. 11 is a sectional view of the device according to FIG. 8 inserted together with an auxiliary device for insertion through skin into a biological body.

The auxiliary device for insertion 6 is almost identical to the one shown in FIG. 4, but the surface of a stopper 6c directly facing the flange surface 2b as shown in FIG. 11 is inclined to the axis of the auxiliary device for insertion 6, correspondingly to the slanting angle θ of the pipe 4 described above. The position of the tip 5a of the auxiliary device for insertion 6 is controlled by the stopper 6c.

After the device is inserted into a biological body, along with the auxiliary device for insertion 6, the auxiliary device 6 is drawn out therefrom.

Figure 12:
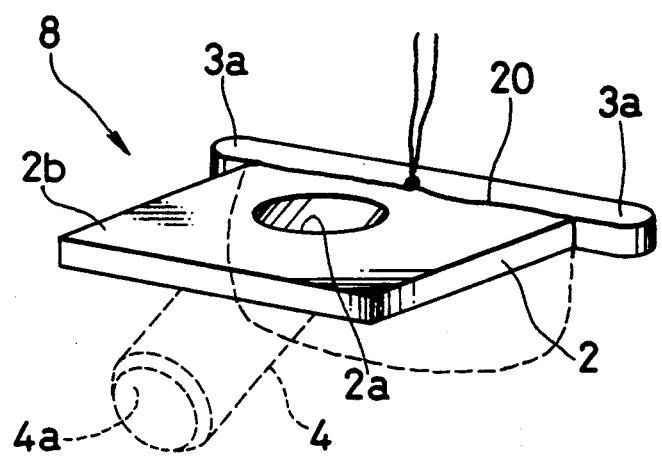
FIG. 12 is a perspective view of the device according to FIG. 8 fixed on skin by means of thread.

As illustrated in FIG. 12, the flange 2 of the device is fixed by means of thread 20.

The device according to a similar embodiment is used in a fat aspirating device identical to the device described in reference to the embodiment and effect and recommended for use in a relatively thin fat layer such as in upper limbs, lower limbs, and gluteal region.

The device in accordance with the present invention is used not only in the fat aspirating device as has been described above, but also it is appropriately used for example in the case of inserting tubes for laparoscopes.

What is claimed is:

1. A transdermal guide for steering a liposuction device in a biological body, said guide comprising:
   a circumferential longitudinal housing extending along an axis and having a distal end tapering axially downwardly;
   a flange mounted on a proximal end of the housing and coaxial therewith, said flange lying in a plane extending at an angle to said axis and being formed with an outer periphery provided with at least two spaced apart formations;
   means formed on said formations for receiving threads fastening said flange to an outer surface of a cutaneous structure of the body, said housing and flange being provided with an inner axial passage opening axially inwardly into a subcutaneous structure upon inserting said guide into the body;
   auxiliary means for inserting said housing into said body, said auxiliary means including:
   an elongated bar-shaped body adapted to be removably inserted into said passage and formed with an inner end tapering axially downwardly and centered on said axis, said bar being slidably displaceable in said guide,
   a stop on said bar body spaced axially outwardly from said inner end, said inner end protruding axially inwardly from said distal end of said housing upon contact of said stop with said flange, and
   a grip extending axially outwardly from said stop and steering said auxiliary means and said housing into said body through the cutaneous and subcutaneous structures thereof until said flange abuts an outer surface of the cutaneous structure.

2. The device defined in claim 1 wherein said grip, stop and bar body formed unitarily.

3. The device defined in claim 1 wherein said angle is 90°.

4. The device defined in claim 1 wherein said angle differs from 90°, said stop bridging said passage upon contact with said flange.

5. The device defined in claim 3 wherein said stop is an annular stop.

6. The device defined in claim 1 wherein said flange, housing and auxiliary means are made of polytetrafluoroethylene.

7. The device defined in claim 6 wherein said flange and housing are integrally molded, said stop, grip and bar body being integrally molded.

8. The device defined in claim 1 wherein said flange, housing and auxiliary means are made of silicone resin.

9. The device defined in claim 1 wherein said inner end of said bar body is substantially frustoconical.

10. A liposuction device for reducing fat in a biological body, said liposuction device comprising:

a circumferential transdermal longitudinal guide extending along an axis and having a distal end adapted to terminate in a subcutaneous structure of the body; a flange mounted on a proximal end of the guide and coaxial therewith, said flange lying in a plane extending at an angle to said axis and being formed with an outer periphery provided with at least two spaced apart formations;

means formed on said formations for receiving threads fastening said flange to an outer surface of a cutaneous structure of the body, said guide and flange being provided with an inner axial passage opening axially inwardly into the subcutaneous structure upon inserting said guide into the body;

auxiliary means for inserting said guide into said body, said auxiliary means including:

an elongated bar-shaped body adapted to be removably inserted into said passage and formed with an inner substantially frustoconical end centered on said axis, said bar being slidably axially displaceable in said guide, stop means for preventing advancement of said bar body into said passage, said inner end protruding axially inwardly from said distal end of said guide upon contact of said stop means with said flange, and a grip extending axially outwardly from said stop means and steering said auxiliary means and said guide into said body through the cutaneous and subcutaneous structures thereof until said flange abuts an outer surface of the cutaneous structure;

a fat aspirating tube adapted to be guided through said passage into said subcutaneous structure upon removal of said auxiliary means, said tube being coaxial with said flange and formed with a plurality of pores provided on a respective distal end of said tube;

reservoir means operatively connected with said tube for collecting the fat from the body; and pump means for aspirating the fat to be evacuated from the body through said pores into said reservoir means.

11. A method of operating a liposuction device, said method comprising the steps of:

providing a transdermal guide having proximal and frustoconical distal ends with a flange formed on said proximal end, said guide and said flange being formed with an axial through passage;

advancing a barshaped body formed with outer and frustoconical inner ends and a stop between said ends into said passage;

thereafter halting advancing of said barshaped body upon reaching a contact between the stop and said flange, an inner end of said body protruding over the distal end of said guide upon halting;

thereafter steering said guide and said barshaped tube with a grip formed on the outer end of said barshaped body, advancing thereby said inner and distal ends in a subcutaneous tissue of the biological body;

thereafter fixing said flange to a skin surface of the biological body;

thereafter removing said barshaped body from said guide;

thereafter inserting a fat aspirating tube into said passage of said guide;

thereafter building up a negative pressure in said aspirating tube thereby aspirating the fat from the subcutaneous layer into a reservoir; and removing said guide upon terminating of aspirating the fat.

* * * * *